US010595755B2

(12) United States Patent
Zalevsky et al.

(10) Patent No.: US 10,595,755 B2
(45) Date of Patent: Mar. 24, 2020

(54) SYSTEM AND METHOD FOR MONITORING GLUCOSE LEVEL (71) Applicant: ContinUse Biometrics Ltd., Tel Aviv (IL)

(72) Inventors: Zeev Zalevsky, Rosh HaAyin (IL); Roy Talman, Herzliya (IL); Yevgeny Beiderman, Tel Aviv (IL); Nisim Nisan Ozana, Rehovot (IL); Javier Garcia, Valencia (ES)

(73) Assignee: CONTINUSE BIOMETRICS LTD., Tel Aviv (IL)

( * ) Notice: Subject to any disclaimer, the term of this patent is extended or adjusted under 35 U.S.C. 154(b) by 182 days.

(21) Appl. No.: 15/945,004

(22) Filed: Apr. 4, 2018

(65) Prior Publication Data

US 2018/0289297 A1 Oct. 11, 2018

Related U.S. Application Data (60) Provisional application No. 62/482,361, filed on Apr. 6, 2017.

(51) Int. Cl.
A61B 5/145 (2006.01)
A61B 5/1455 (2006.01)
G01B 9/02 (2006.01)
A61B 5/00 (2006.01)
A61B 5/1495 (2006.01)
A61B 5/024 (2006.01)

(52) U.S. Cl.
CPC ........ A61B 5/14532 (2013.01); A61B 5/0066 (2013.01); G01B 9/02094 (2013.01); A61B 5/0064 (2013.01); A61B 5/02405 (2013.01); A61B 5/1455 (2013.01); A61B 5/1495 (2013.01)

(58) Field of Classification Search
CPC . A61B 5/1455; A61B 5/14532; A61B 5/0066; A61B 5/7271
See application file for complete search history.

(56) References Cited

U.S. PATENT DOCUMENTS

| 8,638,991 | B2 | 1/2014 | Zalevsky et al. | |
|---|---|---|---|---|
| 2009/0209834 | A1* | 8/2009 | Fine | A61B 5/14551 600/316 |
| 2013/0144137 | A1* | 6/2013 | Zalevsky | A61B 5/14546 600/310 |
| 2014/0148658 | A1 | 5/2014 | Zalevsky et al. | |
| 2017/0068790 | A1* | 3/2017 | Fuerst | G16H 40/67 |

* cited by examiner

Primary Examiner — Eric F Winakur
(74) Attorney, Agent, or Firm — Browdy and Neimark, PLLC (57) ABSTRACT A system for monitoring glucose blood level of a user is disclosed. The system comprising an illumination unit configured for providing coherent optical illumination on a selected inspection region on the user body, a collection unit configured for collecting light returning from the inspection region and generating a plurality of image data pieces associated with speckle patterns in the collected light, and a control unit comprising a processing utility and storage utility comprising pre-stored calibration data, the processing utility is configured for receiving input data on a plurality of image data pieces from the collection unit and for processing said input data for determining correlation functions between different image data pieces and using said correlation functions and said pre-stored calibration data for determining data on glucose blood level of the user.

3 Claims, 5 Drawing Sheets

SYSTEM AND METHOD FOR MONITORING GLUCOSE LEVEL

TECHNOLOGICAL FIELD

The present invention relates to a system and a method for use in determining one or more biological parameters of a subject. The technique of the invention is especially relevant for measurement of glucose concentration in subject's blood.

BACKGROUND

Diabetes mellitus is a groups of diseases associated with regulation of sugar blood (typically glucose concentration) levels. Various pharmacological and non-pharmacological treatments are known, however periodic monitoring of blood sugar levels provides effective, long-term, supporting treatment and may enable relatively normal day-to-day life.

Various techniques are known for monitoring glucose blood levels, most of these techniques require invasive measurements, e.g. by drawing a drop of blood for direct measurement of glucose levels. Lately, various non-invasive techniques have been devised in the field of measuring blood-related parameters, such as glucose level and others. The existing non-invasive techniques include impedance-based techniques as well as optical measurement techniques. For example, in glucose meters based on near infrared spectroscopy, a tissue is illuminated with light in the infrared spectrum, and one or both light reflected by the tissue and light transmitted through the tissue are measured. The portion of light that is reflected and/or transmitted is indicative of the blood glucose level. Such glucose meters are used for tissue investigation in different depths varying from 1 to 100 millimeters or 10 to 50 micrometers.

Some glucose meters use Raman spectroscopy to measure scattered light that has been influenced by the oscillation and rotation caused by glucose. Glucose meters based on photo-acoustic spectroscopy measure parameters of an acoustic pressure wave created by rapid heating of the sampled area. Other glucose meters measure changes in the scattering and the polarization parameters of light caused by glucose. Femtosecond pulse interferometry can be used to determine glucose concentration, by measuring the group refraction index of a glucose solution using a time delay of femtosecond order in a time-of-flight method. Optical coherence tomography can be used to measure and analyze the interference pattern between the coherently backscattered light from specific layers of tissues and a reference beam.

Optical techniques for monitoring and measuring various parameters of a sample, including blood related parameters have been described. Such techniques include:

US2014148658 presents a system and method for use in monitoring one or more conditions of a subject's body. The system comprises a control unit which comprises an input port for receiving image data and data indicative of at least one external stimulation (external field) applied to a portion of the subject's body during collection of the image data therefrom, a memory utility, and a processor utility. The image data is indicative of a sequence of speckle patterns generated by the portion of the subject's body according to a certain sampling time pattern. The processor utility is configured and operable for carrying out the following: processing the image data utilizing the data indicative of the applied external field(s), said processing comprising determining a spatial correlation function between successive speckle patterns in the sequence, and determining a time varying spatial correlation function in the form of a time-varying function of at least one feature of the correlation function indicative of a change of the speckle pattern over time; selecting at least one parameter of the time-varying spatial correlation function, and applying to said at least one parameter one or more of the models to determine one or more corresponding body conditions; and generating output data indicative of said one or more corresponding body conditions.

U.S. Pat. No. 8,638,991 presents a method for imaging an object. The method comprises imaging a coherent speckle pattern propagating from an object, using an imaging system being focused on a plane displaced from the object.

General Description

As indicated above, optical monitoring may provide non-invasive and efficient techniques for determining and observing parameters of a patient. Further, the use of coherent illumination and detection of variation in secondary speckle patterns generated in light returning from an inspection region of the patient (herein referred to as speckle-based detection) can be used for measurement of various biophysical parameters and provide robust and simple monitoring technique.

The present invention utilizes such speckle-based optical monitoring for simplifying routine monitoring of glucose levels in user's blood, enabling effectively continuous monitoring of glucose levels while limiting the need for invasive blood sampling. To the end the technique of the present invention utilizes detection of correlations between image data pieces associated with speckle patterns in light returning from an inspection region on the user's body, for continuously determining data about heart rate of the user; and utilizing the heart rate data in accordance with pre-provided calibration data connecting heart rate variability with varying levels of glucose in the user's blood.

The technique of the present invention, is based on speckle-based monitoring, where correlation functions between speckle patterns collected in different (consecutive) image data pieces are used for obtaining data about physical/mechanical movement of the inspection region. More specifically, variation in location or orientation of at least a part of the inspection region affect arrangement of the so-collected speckle patterns and can thus be detected based on correlation between speckle patterns. The technique of the invention utilizes detection of vibrations associated with blood pulsating due to heart beats and resulting in periodic vibration pulses that may be detected from effectively any selected location (inspection region) on the body. Based on the heart rate data detected using the speckle-based monitoring, the present technique utilizes determining at least one variability parameter indicative of variations in the heart rate of the user, for determining data on variations in glucose concentration of the user.

The present invention generally provides a system for monitoring glucose levels, according to some embodiments of the invention the system comprising a light source unit configured for providing coherent optical radiation and directing it onto a selected inspection region on a user's body (e.g. hand, arm etc.), a collection unit configured for collecting light returning by reflection and/or scattering from the inspection region and generate a plurality of image data pieces associated with secondary speckle patterns formed by light interference, and a control unit. The collection unit comprises an imaging lens arrangement and a detector array located at a selected distance from the imaging lens arrangement such that and image formed on the detector array by the imaging lens arrangement corresponds with an intermediate plane located in optical path of light propagation from the inspection region toward the collection unit.

The control unit is configured and operable for receiving input data comprising a plurality of image data pieces, each indicative of a detected speckle pattern, and processing the input data in accordance with pre-stored calibration data for determining data on glucose levels in user's blood. The control unit typically comprises a processing utility, storage utility (e.g. memory unit) and input port for receiving data from the collection unit and output port (e.g. network communication and/or user interface). The processing utility comprises hardware/software modules such as correlation module configured for determining correlation between consecutive speckle patterns in image data pieces, heart rate module configured for processing data on the correlation functions and determine accordingly data on heart rate of the user, HRV module configured for determining heart rate variability measure based on heart rate data, and glucose module configured for utilizing heart rate variability measure and pre-stored calibration data, stored at the storage utility, for determining data on glucose concentration in user's blood. The control unit may then generate user indication data indicative of glucose levels and provide it to the user or selected physician. Additionally, the data on glucose levels may be stored for monitoring and additional processing.

Thus, according to a broad aspect, the present invention provides a system for monitoring glucose blood level of a user, the system comprising an illumination unit configured for providing coherent optical illumination on a selected inspection region on the user body, a collection unit configured for collecting light returning from the inspection region and generating a plurality of image data pieces associated with speckle patterns in the collected light, and a control unit comprising a processing utility and storage utility comprising pre-stored calibration data, the processing utility is configured for receiving input data on a plurality of image data pieces from the collection unit and for processing said input data for determining correlation functions between different image data pieces and using said correlation functions and said pre-stored calibration data for determining data on glucose blood level of the user.

According to some embodiments, the processing utility may comprise one or more processors comprising: correlation module configured for receiving plurality of image data pieces and for determining correlations between consecutive image data pieces and generating at least one time correlation function associated with variation between speckle patterns in said plurality of image data pieces; heart rate module configured for receiving data on said at least one time correlation function and applying one or more selected filters for determining heart rate data of the user from said at least one time correlation function; heart rate variability (HRV) module configured for receiving said heart rate data over selected measurement time and determining at least one variability parameter indicative of variation in heart rate of the user within the measurement time; and glucose module configured for receiving said at least one variability parameter and determining data on glucose concentration in blood of the user in accordance with pre-stored calibration data and said at least one variability parameter.

According to one other broad aspect, the present invention provides a system for monitoring glucose blood level of a user, comprising a processing utility, storage utility comprising pre-stored calibration data and input port configured for receiving input data in the form of a plurality of image data pieces associated with speckle patterns collected from a selected inspection region; the processing utility comprising: correlation module configured for receiving said plurality of image data pieces and determining correlation functions between consecutive speckle patterns, heart rate module configured receiving and processing said correlation functions and determining heart rate data therefrom, HRV module configured for receiving heart rate data from the heart rate module and processing the heart rate data for determining heart rate variability measure, and a glucose module configured for processing said heart rate variability measure in accordance with calibration data stored in the storage utility and determining data about glucose blood level of the user.

According to yet another broad aspect, the present invention provides a software product embedded on a non-transitory computer readable medium and comprising computer readable instructions that when executed by one or more processors causing the processor to:

being responsive to obtain one or more sequences of image data piece, each comprising at least one pattern of secondary speckles collected from an inspection region on a user;

processing the one or more sequences of image data piece for determining at least one time correlation function indicative of variations between speckle patterns in the sequence of image data pieces;

filtering said at least one time correlation function for determining variations associated with heart rate activity and determining heart rate variability measure being indicative of frequency variations of said heart rate activity within selected monitoring period;

obtaining, from a storage utility, calibration data indicative of glucose levels of the user and determining current glucose level in accordance with said heart rate variability measure; and generating indication on current glucose measure.

According to yet further broad aspect, the present invention provides a method for use in determining glucose levels of a subject, the method comprising: providing one or more sequences of image data piece, each comprising at least one pattern of secondary speckles collected from an inspection region on a user; processing, by a computer processor, the one or more sequences of image data piece for determining at least one time correlation function indicative of variations between speckle patterns in the sequence of image data pieces; filtering said at least one time correlation function for determining variations associated with heart rate activity and determining heart rate variability measure being indicative of frequency variations of said heart rate activity within selected monitoring period; obtaining, from a storage utility, calibration data indicative of glucose levels of the user and determining current glucose level in accordance with said heart rate variability measure; and generating indication on current glucose measure.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
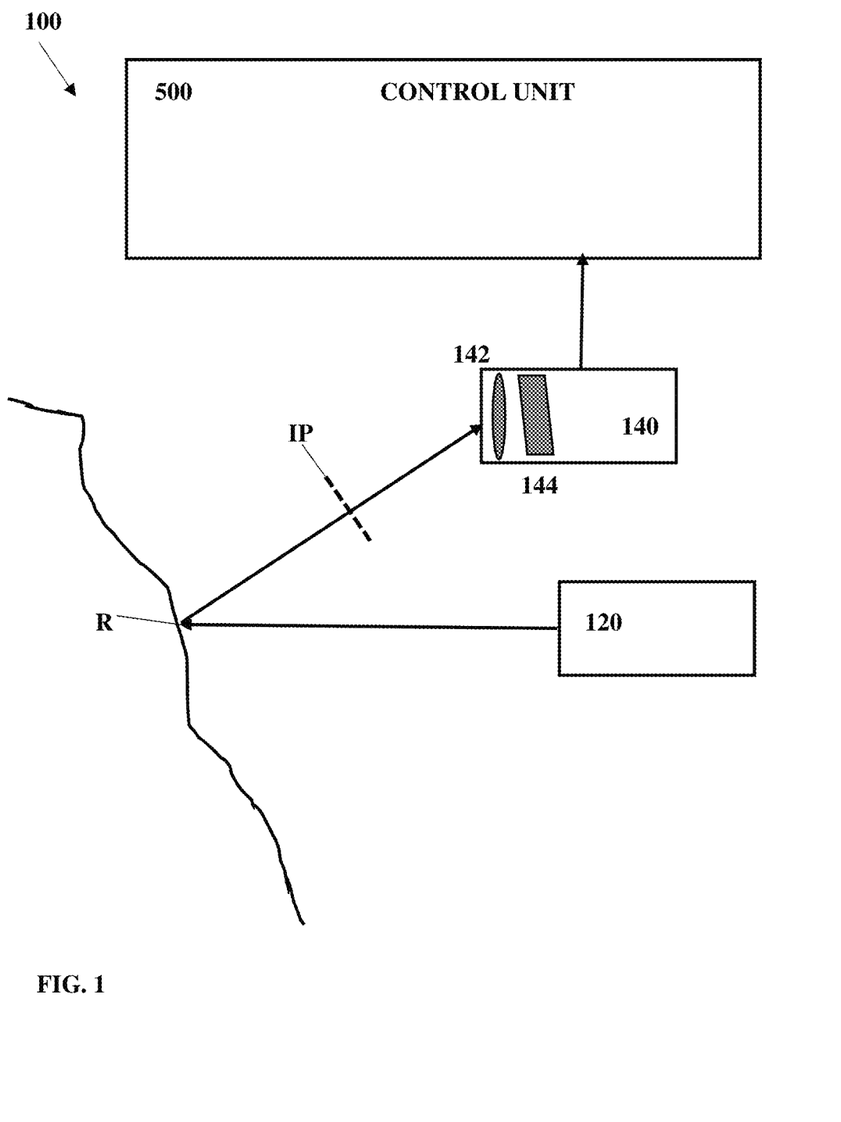
FIG. 1 schematically illustrates a system for determining glucose level in user's blood.

As indicated above, the technique of the present invention utilizes speckle-based monitoring of a user/patient's body and pre-provided calibration data for determining data indicative of glucose levels in the user's blood. Reference is made to FIG. 1 schematically illustrating a system 100 according to some embodiments of the invention. System 100 includes an illumination unit 120 configured for providing and directing coherent illumination of a selected wavelength range onto a selected inspection region R on the user and a collection unit 140 configured for collecting light returning from the inspection region R and generating a plurality of image data pieces associated with speckle patterns formed by self-interference of the returning light. Additionally, system 100 includes a control unit 500 configured for receiving input data including plurality of image data pieces from the collection unit 140, and for processing the input data in accordance with pre-stored calibration data for determining data about glucose levels of the user's blood.

The illumination unit 120 may typically include a laser unit, e.g. diode laser, and may also include an optical arrangement for directing the illumination beam onto the inspection region R to provide selected illumination spot size. The collection data 140 generally includes an imaging lens arrangement 142 and a detector array 144. The imaging lens arrangement 142 and detector array 144 of the collection unit 140 are arranged for collection of defocused images with respect to the inspection region R. More specifically, the imaging lens arrangement and the detector array are located such that the optical plane of the detector array, being image plane, corresponds to an optical plane (object plane) that is axially shifted with respect to the plane of the inspection region. For example, the collection unit is configured for collection of images associated with imaging certain intermediate plane IP located in optical path of light returning from the inspection region R, or being further from the inspection region R. Accordingly, so-generated image data includes at least a secondary speckle pattern formed by interference of light components reflected/scattered from the inspection region. Generally the collection unit 140, of the detector array thereof, is configured for collection of image data pieces at a selected frame rate generating sufficient rate of data for determining heart rate activity of the user. For example, the collection unit 140 may be operated for generating effective frame rate between 80 and 400 frames per second, enabling detection of heart rate between 40 and 200 respectively.

The collection unit 140 is further configured and operable for transmitting so-generated plurality of image data pieces to the control unit 500 for processing and determining data about glucose levels. The control unit 500 is illustrated in more detail in FIG. 2 and typically includes a processing utility 510 including one or more processors, input port 520 for receiving input data from the collection unit 140, storage utility 580 for storing pre-provided calibration data, and output/UI utility 590. The processing utility 510 is configured and operable for processing input data, being in the form of a plurality of image data pieces associated with speckle patterns, in accordance with pre-provided calibration data stored in the storage utility 580. To this end the processing utility 510 includes hardware and/or software modules configured for performing certain processing actions.

Figure 2:
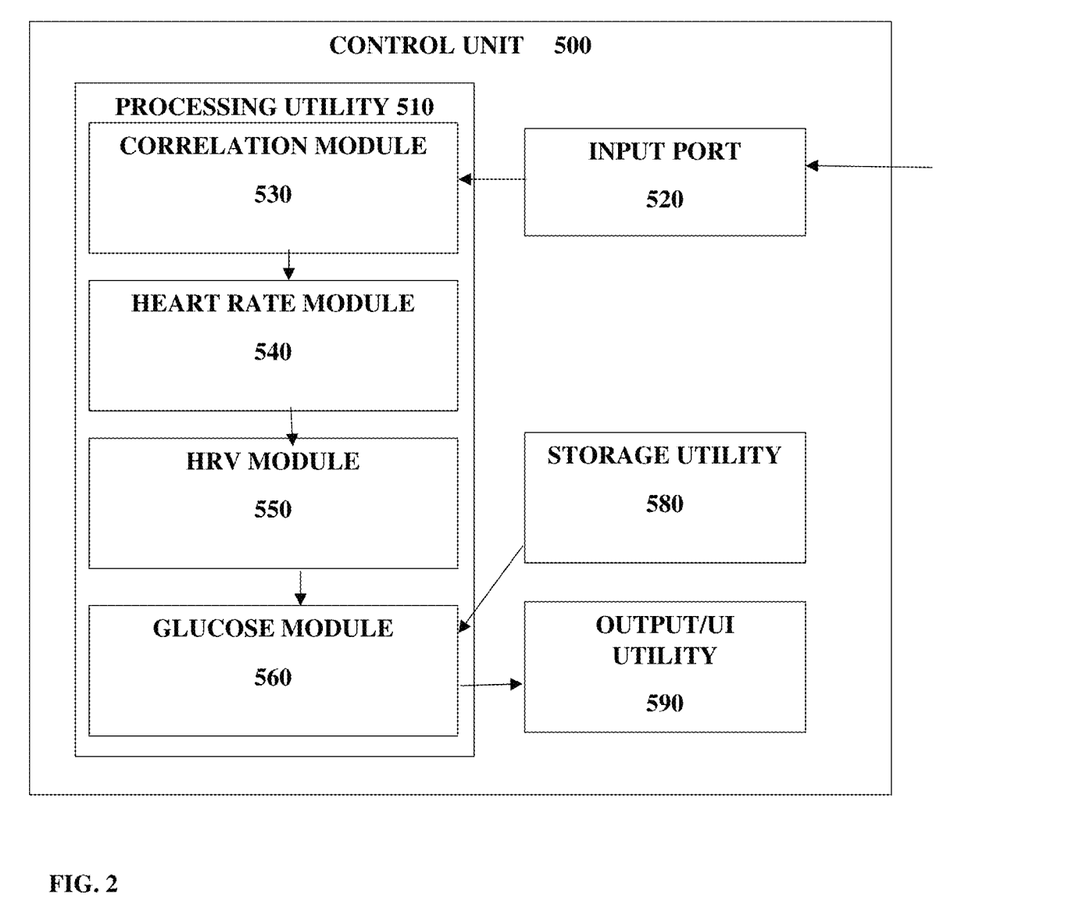
FIG. 2 illustrates a schematic configuration of a control unit according to some embodiments of the invention.

As shown in FIG. 2, the processing utility 510 may include a correlation module 530, heart rate module 540, HRV module 550 and glucose module 560. The correlation module 530 is configured and operable for processing image data pieces and determining correlation function based on correlations between speckle patterns in the image data pieces. Typically, the correlation module 530 determines correlation between each two consecutive image data pieces, providing one or more time-correlation functions associated with monitoring period in which a plurality of image data pieces are acquired. The correlation module 530 may operate in real-time or almost real time such that the correlation functions are determined as input image data pieces are received from the collection unit 140. The correlation module 530 thus generates at least one correlation function (e.g. spatial correlation function, and/or X axis and Y axis correlation functions) indicating variations in location, orientation and/or curvature of the inspection region R. Accordingly, the at least one correlation function is indicative of vibrations of the inspection region R, provided at sampling rate corresponding with frame rate of the collection unit 140.

The heart rate module 540 is configured and operable for receiving data on the at least one correlation function from the correlation module 530, and processing the correlation functions' data to determine vibration data associated with heart rate of the user. As indicated above, the correlation functions between the collected image data pieces are indicative of variations in location and/or orientation of the inspection region. Accordingly, any vibrations in the inspection region may be identified in the correlation functions provided by the correlation module 530. The heart rate module 540 may utilize one or more predetermined filters associated with frequency and repetition of correlation variations for identifying heart rate operation data. For example, heart rate of a user may generally be between 40 bpm and 200 bpm and is typically between 60 bpm and 90 bpm. Further repeating pulses are relatively similar between them. Thus, the heart rate module 540 filters out vibrations that are not associated with heart rate operation from the correlation function, and transmits data about heart rate operation to the HRV module 550. It should be noted that the heart rate data may also be stored in the storage utility 580, and/or further processed to determine additional information about the user.

The HRV module 550 is configured and operable for receiving data on heart rate from the heart rate module 540 and for determining heart rate variability measure according to variations in heart rate. Generally, heart rate variability (HRV) is an existing physiological phenomenon where the beat to beat interval in heart rate changes between high frequency (HF) periods and low frequency (LF) periods. Heart rate variability may be associated with various physiological mechanisms including respiratory cycle and others, as well as glucose blood levels. The HRV module 550 may be configured for determining HRV measure using generally any one of various methods including time-domain techniques counting variation in beat to beat intervals; frequency-domain technique analyzing beat associated with determined high frequency (HF) band and low frequency (LF) band; as well as geometrical, linear and non-linear techniques.

Generally, heart rate variability measures are determined within selected time period. More specifically, the present technique may utilize monitoring periods of 10-30 seconds, 30 seconds to two minutes, or 1-5 minutes. In this connection, the heart rate variability data can be determined by determining frequency of heart rate within time windows of 5-60 seconds, or 5-20 seconds, wherein in each window the heart rate frequency is determined. High and low frequencies determined within the monitoring period are identified for determining ratio between the high frequency and low frequency of detected heart rate. In some embodiments, the technique may also identify various types of heart arrhythmia. For example, the HRV module may be configured and operable for generating an alert to a user in one or more of the following cases: variation between high and low frequency measures exceeds a selected threshold; heart rate frequency is not determined within time window of 10 seconds indicating arrhythmic operation of the heart; high and/or low frequencies of heart rate exceed selected rate limits (e.g. heart rate exceeds 180 bpm, or is lower than 40 bpm).

The glucose module 560 is configured for receiving data on HRV measure from the HRV module 550 and for obtaining corresponding correlation data from the storage utility 580 for determining an estimated glucose-blood level. The data about glucose-blood levels is typically provided as output through the user interface 590, and/or is stored or further processed in the storage utility 580 or remote location. Generally, if the glucose levels exceed one or more predetermined threshold, the user interface utility 590 may be operated for raising a suitable alert and/or contacting a preselected physician to optimize treatment when needed.

Figure 3:
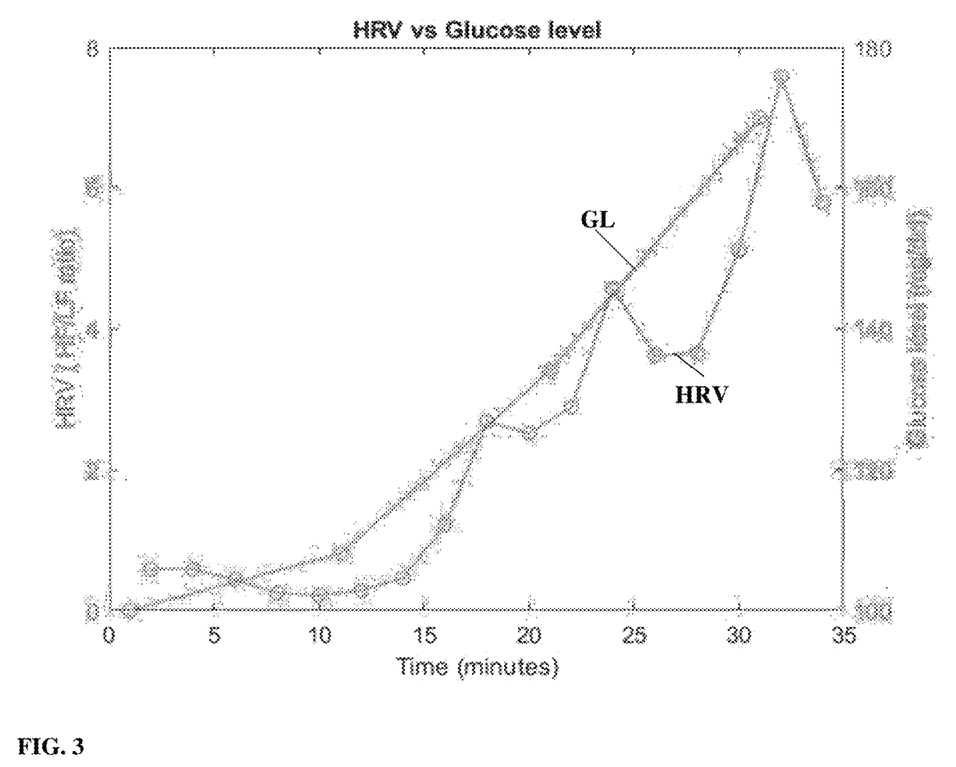
FIG. 3 shows experimentally measured data about correlation between heart rate variability determined by processing of speckle-based collected data and glucose levels.

Reference is made to FIG. 3 showing experimentally measured calibration data associated measured heart rate variability HRV as ratio between high and low frequency periods (HF/LF ratio) and glucose concentration as measured in the conventional techniques by measuring a drop of blood extracted from the user. In this exemplary correlation data, the user's glucose levels were intentionally increased by consumption of high glucose drink within a period of 35 minutes. During the selected period, the user's glucose levels were periodically measured using a conventional technique. Additionally, HRV data was optically measured using the above described technique. As shown, a strong correlation between HRV data and glucose levels is verified providing a calibration data enabling glucose monitoring using the above described technique.

Figure 4:
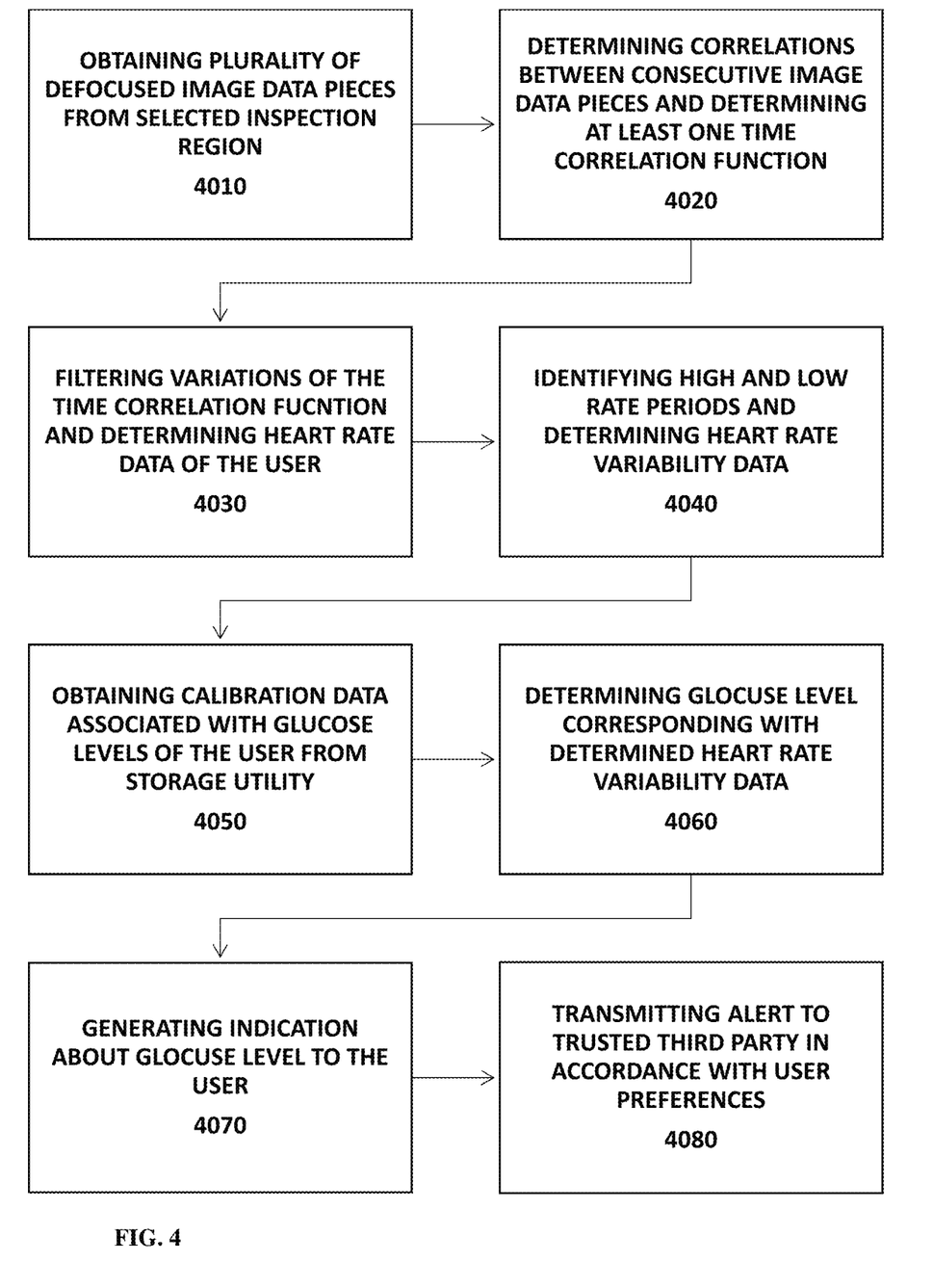
FIG. 4 shows a flow diagram illustrating a technique for determining glucose concentration according to some embodiments of the invention.

Reference is made to FIG. 4 illustrating an example of a technique for determining glucose concentration of the user according to some embodiments of the invention. As shown the technique includes obtaining or providing a sequence of image data pieces associated with defocused imaged of a selected inspection region on the user's body 4010. Generally as indicated above, the image data pieces are obtained when the inspection region is illuminated with coherent illumination of a selected wavelength range (e.g. using laser illumination). The image data piece are preferably collected by defocused imaging as described above to enable detection of secondary speckle patterns in the image data pieces. The so-obtained sequence of image data piece is provided for processing, e.g. by one or more computer processor executing computer readable instructions according to some embodiments of the present technique, for determining one or more parameters of the user including glucose concentration level. The processing includes determining correlations between consecutive image data pieces and determining at least one time correlation function 4020 being associated with correlations between the collected speckle patterns. Filtering the time correlation function(s) using one or more selected filters 4030 (e.g. frequency band filtering) for determining repetitive vibrations associated with heart rate of the user. Processing the heart rate sequence and determining high and low frequency periods 4040. Such periods are determined as time periods where the heart rate is above a determined average rate, and time periods where the heart rate is below the determined average heart rate. Based on the high and low frequency levels, a measure for heart rate variability HRV is determined.

The association between HRV data and glucose levels is provided via a user-related calibration data. To this end the technique utilizes pre-stored calibration data 4050 including data on glucose levels as measured to the user and corresponding HRV valued. The calibration data may also include HRV values for one or more activity modes of the user, e.g. walking, house work, sitting, resting etc. Based on the calibration data and the determined HRV data, the technique can determine glucose level of the user 4060. The glucose level data is provided to the user 4070 and proper indications may be transmitted to one or more trusted third parties 4080 in accordance with user preferences and for enabling emergency response when needed.

Figure 5:
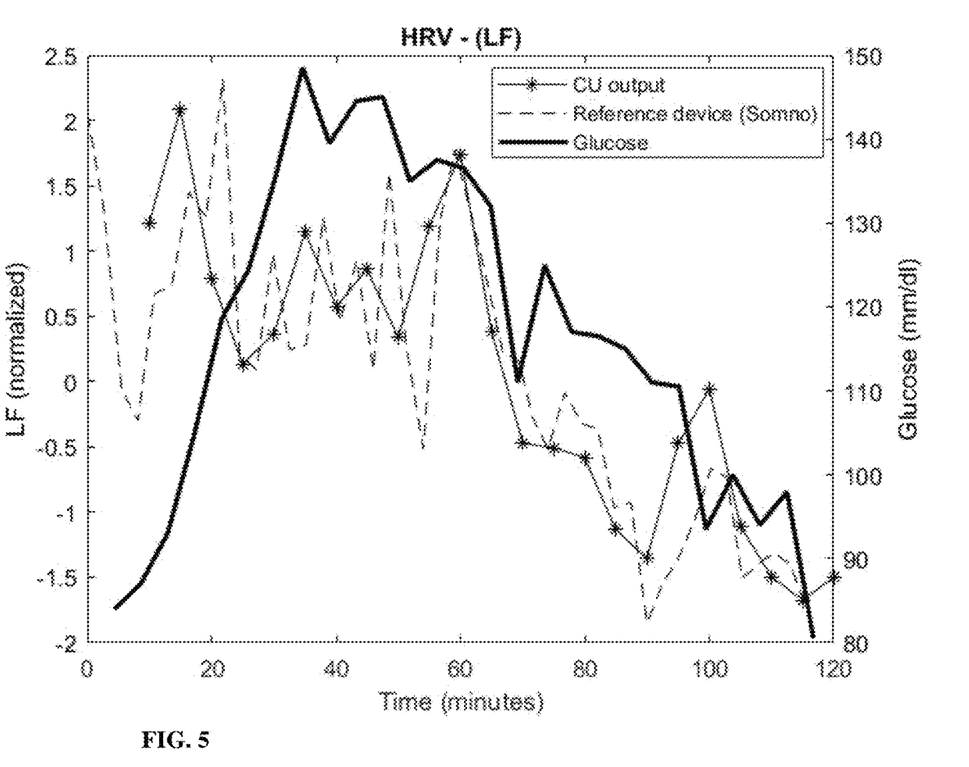
FIG. 5 shows experimental results of determining glucose concentration in accordance with the present technique.

Reference is made to FIG. 5 showing experimental results of determining glucose concentration in accordance with the present technique. FIG. 5 shows a plot indicating heart rate variability (LF) measured by the speckle-based monitoring of the present technique (CU output) and using a reference heart monitoring unit SOMNOtouch™ NIBP commercially available from SOMNOmedics, the plot also shows blood glucose concentration as measured by the conventional technique to the test subject. During the test, the subject was sitting still on a chair and recorded using speckle-based monitoring technique as described above acquiring chest speckle signal. The reference was device provided additional heart rate monitoring. Glucose level was measured using conventional glucose-meter at periods of ten minutes.

To experience glucose variations, the subject was given a glucose dose ten minutes after beginning of the test. This is shown by increase in glucose level until about 35 minutes into the test. In accordance with biological operation of the subject, the glucose level dropped naturally after about 35 minutes during the test.

The speckle-based monitoring, as well as the reference heart rate device provide heart rate data. The heart rate data was processed for identifying S1 peaks indicative of heart pulses and for determining S1-S1 intervals. Heart rate variability was determined utilizing nonparametric Fourier transform applied on the S1-S1 interval data, being a time-series graph. The HRV frequency band obtained is the low-frequency (LF) power (0.04-0.15 Hz). The HRV scale shows in FIG. 5 is normalized for simplicity.

As shown from FIG. 5, the normalized LF-HRV data obtained both using the speckle-based monitoring technique and by the reference device provided high correlation level between them. Variations in glucose levels are shown to be associated with variation in HRV, the lowering glucose levels are correlation with dropping of the HRV-LF. Accordingly, the present invention provides non-invasive technique enabling continuous monitoring of glucose levels in accordance with no more than periodic calibration.

Generally, the present technique may be operated as computer software executed on computer system being stationary or mobile and configured for monitoring a user periodically or in response to user initiated command. The computer system may be associated with a light source unit and camera unit configured for enabling collection of the defocused image data pieces, e.g. being attachment to smartphone unit and using the internal smartphone camera.

It should generally be noted that glucose monitoring is typically associated with chronic diabetes condition of the user. Accordingly generating calibration data may be suitable for such users enabling at least a level of alert provided by remote monitoring, and reducing the need for periodical invasive measurements.

The invention claimed is:

1. A system for monitoring glucose blood level of a user, the system comprising
    an illumination unit configured for providing coherent optical illumination on a selected inspection region on the user body,
    a collection unit configured for collecting light returning from the inspection region and generating a plurality of image data pieces associated with speckle patterns in the collected light, and
    a control unit comprising a processing utility and storage utility comprising pre-stored calibration data, the processing utility is configured for receiving input data on a plurality of image data pieces from the collection unit and for processing said input data for determining correlation functions between different image data pieces and using said correlation functions and said pre-stored calibration data for determining data on glucose blood level of the user,
    wherein said processing utility comprises one or more processors comprising: a correlation module configured for receiving said plurality of image data pieces and for determining correlations between consecutive image data pieces and generating at least one time correlation function associated with variation between speckle patterns in said plurality of image data pieces; a heart rate module configured for receiving data on said at least one time correlation function and applying one or more selected filters for determining heart rate data of the user from said at least one time correlation function; a heart rate variability (HRV) module configured for receiving said heart rate data over selected measurement time and determining at least one variability parameter indicative of variation in heart rate of the user within the measurement time; and a glucose module configured for receiving said at least one variability parameter and determining data on glucose concentration in blood of the user in accordance with pre-stored calibration data and said at least one variability parameter.

2. A system for monitoring glucose blood level of a user, comprising a processing utility, a storage utility comprising pre-stored calibration data and an input port configured for receiving input data in the form of a plurality of image data pieces associated with speckle patterns collected from a selected inspection region; the processing utility comprising: a correlation module configured for receiving said plurality of image data pieces and determining correlations between consecutive speckle patterns and generating at least one time correlation function associated with variation between speckle patterns, a heart rate module configured for receiving and processing said at least one time correlation function[s] and determining heart rate data therefrom, a HRV module configured for receiving heart rate data from the heart rate module and processing the heart rate data for determining a heart rate variability measure, and a glucose module configured for processing said heart rate variability measure in accordance with calibration data stored in the storage utility and determining data about glucose blood level of the user.

3. A software product embedded on a non-transitory computer readable medium and comprising computer readable instructions that when executed by one or more processors causing the processor to:
    being responsive to obtain one or more sequences of image data piece, each comprising at least one pattern of secondary speckles collected from an inspection region on a user;
    processing the one or more sequences of image data piece for determining correlations between consecutive speckle patterns and generating at least one time correlation function indicative of variations between speckle patterns in the sequence of image data pieces;
    filtering said at least one time correlation function for determining variations associated with heart rate activity and determining a heart rate variability measure being indicative of frequency variations of said heart rate activity within selected monitoring period;
    obtaining, from a storage utility, calibration data indicative of glucose levels of the user and determining current glucose level in accordance with said calibration data and said heart rate variability measure; and
    generating an indication of the current glucose measure.

* * * * *